United States Patent [19]

Bening et al.

[11] Patent Number: 5,391,663
[45] Date of Patent: Feb. 21, 1995

[54] PROTECTED FUNCTIONAL INITIATORS FOR MAKING TERMINALLY FUNCTIONALIZED POLYMERS

[75] Inventors: Robert C. Bening, Katy; Carl L. Willis, Houston, both of Tex.

[73] Assignee: Shell Oil Company, Houston, Tex.

[21] Appl. No.: 155,665

[22] Filed: Nov. 22, 1993

[51] Int. Cl.$^6$ .......................... C07F 7/18; C08F 4/46
[52] U.S. Cl. .................................. 526/178; 525/338; 525/353; 525/383; 525/385
[58] Field of Search ................ 526/178; 525/338, 353, 525/383, 385

[56] References Cited
FOREIGN PATENT DOCUMENTS 2241239 8/1991 United Kingdom .
91/12277 8/1991 WIPO .

Primary Examiner—Joseph L. Schofer
Assistant Examiner—N. Sarafim
Attorney, Agent, or Firm—Keith M. Tackett

[57] ABSTRACT

The anionic polymerization of unsaturated monomers with functionalized initiators having the structure $R^1R^2R^3Si$—O—A'—Li is improved by selecting A' from the structures —$CH_2$—$CH_2$—$CH_2$—(1,3-propyl), —$CH_2$—$CH(CH_3)$—$CH_2$—(2-methyl-1,3-propyl), —$CH_2$—$C(CH_3)_2$—$CH_2$—(2,2-dimethyl-1,3-propyl), or —$CH_2$—$CH_2$—$CH_2$—$CH_2$—$CH_2$—$CH_2$—$CH_2$—$CH_2$—(1,8-octyl). This narrow class of polymerization initiators operate at surprisingly higher polymerization temperatures with surprisingly lower amounts of dead initiator than similar initiators wherein A' is —$CH_2$—$CH_2$—$CH_2$—$CH_2$—(1,4-butyl), —$CH_2$—$CH_2$—$CH_2$—$CH_2$—$CH_2$—(1,5-pentyl), or —$CH_2$—$CH_2$—$CH_2$—$CH_2$—$CH_2$13 $CH_2$—(1,6-hexyl).

12 Claims, No Drawings

PROTECTED FUNCTIONAL INITIATORS FOR MAKING TERMINALLY FUNCTIONALIZED POLYMERS

FIELD OF THE INVENTION

This invention relates to anionic polymerization of monomers and to functionalized polymers used as components in adhesives, sealants and coatings.

BACKGROUND OF THE INVENTION

Anionic polymerization of conjugated dienes with lithium initiators, such as sec-butyllithium, and hydrogenation of residual unsaturation has been described in many references including U.S. Pat. No. Re. 27,145 which teaches a relationship between the amount of 1,2-addition of butadiene and the glass transition temperatures of the hydrogenated butadiene polymers.

The capping of living anionic polymers to form functional end groups is described in U.S. Pat. Nos. 4,417,029, 4,518,753, and 4,753,991. Of particular interest for the present invention are anionic polymers that are capped on one or more ends with hydroxyl, carboxyl, phenol, epoxy, and amine groups.

Anionic polymerization using protected functional initiators having the structure $R^1R^2R^3Si-O-A'-Li$ is described in WO 91/12277 wherein $R^1$, $R^2$, and $R^3$ are preferably alkyl, alkoxy, aryl, or alkaryl groups having from 1 to 10 carbon atoms, and $A'$ is preferably a branched or straight chain bridging group having at least 2 carbon atoms. The bridging group is most preferably a straight chain alkyl having from 3 to 10 carbon atoms and is exemplified by the following compound:

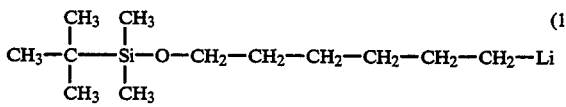

(1)

which is readily prepared by lithiation of the reaction product of 1-chloro-6-hydroxy-n-hexane and t-butyldimethylchlorosilane. The use of such an initiator as Structure (1) to polymerize the desired monomer(s), followed by capping to produce the second terminal alcohol group, has several advantages over the preparation of telechelic diols by capping polymers prepared with difunctional initiators such as 1,4 dilithiobutane and lithium naphthalide. In addition to providing the option of polymerizing in non-polar solvents, this route avoids the formation of ionic gels, which are known to occur when diinitiated polymers are capped with reagents such as ethylene oxide, generating the polymeric di-alkoxide. These gels form even in relatively polar solvent mixtures and greatly complicate subsequent processing steps. By capping to produce the alkoxide on only one polymer terminus, these gels are avoided.

The initiator of Structure (1) anionically polymerizes unsaturated monomers like conventional lithium initiators but starts the polymer chain with a t-butyldimethylsiloxy functional group that can be readily converted to a primary alcohol, which is useful in a variety of subsequent reactions. While it appears that the majority of Structure (1) is active if the initiation step is performed at a low temperature ($-5°$ C.), at slightly higher temperatures, a significant fraction of the initiator charge fails to initiate polymerization; a large portion of the initiator is non-reactive or "dead". Initiation with sec-butyllithium occurs efficiently well above room temperature. Nevertheless, the active portion of the initiator of Structure (1) produces living polymers that can be further endcapped and hydrogenated like conventional anionic polymers.

It is an object of the present invention to provide improved protected functional initiators that operate efficiently (with a minimum of dead initiator) at economical temperatures. It is also an object of this invention to make functionalized anionic polymers having terminal functional groups on one or more ends of the polymer molecules.

SUMMARY OF THE INVENTION

The present invention is the discovery that lithium initiators having the structure:

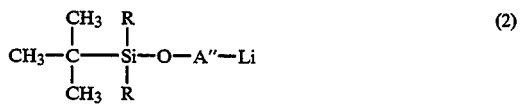

(2)

wherein each R is methyl, ethyl, n-propyl, or n-butyl and $A''$ is an alkyl-substituted or non-substituted propyl bridging group, including $-CH_2-CH_2-CH_2-$ (1,3-propyl), $-CH_2-CH(CH_3)-CH_2-$ (2-methyl-1,3-propyl) and $-CH_2-C(CH_3)_2-CH_2-$ (2,2-dimethyl-1,3-propyl), or an alkyl-substituted or non-substituted octyl bridging group, including $-CH_2-CH_2-CH_2-CH_2-CH_2-CH_2-CH_2-CH_2-$ (1,8-octyl), initiate polymerization of anionic polymers at surprisingly higher polymerization temperatures With surprisingly lower amounts of dead initiator (higher efficiency) than similar initiators wherein $A''$ is replaced by alkyl-substituted or non-substituted butyl, pentyl, or hexyl bridging groups, such as $-CH_2-CH_2-CH_2-CH_2-$1,4-butyl), $-CH_2-CH_2-CH_2-CH_2-CH_2-$(1,5-pentyl), or $-CH_2-CH_2$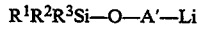 $CH_2-CH_2-CH_2-CH_2-$(1,6-hexyl). Another aspect of this invention is that the polymers produced by these initiators are readily endcapped and hydrogenated prior to removal of the silyl group to form anionic polymers having one or more terminal functional groups under commercially-attractive conditions.

DETAILED DESCRIPTION OF THE INVENTION

The anionic polymerization of unsaturated monomers with functionalized initiators having the structure $$R^1R^2R^3Si-O-A'-Li$$

is described in WO 91/12277 wherein $R^1$, $R^2$ and $R^3$ are preferably alkyl, alkoxy, aryl, or alkaryl groups having from 1 to 10 carbon atoms, and $A'$ is preferably a branched or straight chain bridging group having at least 2 carbon atoms, preferably linear alkyls having from 3 to 10 carbon atoms.

The present invention is the discovery that lithium initiators having the structure:

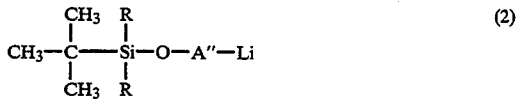

(2)

wherein each R is methyl ethyl, n-propyl, or n-butyl and $A''$ is an alkyl-substituted or non-substituted propyl bridging group, including —CH₂—CH₂—CH₂—(1,3-propyl), —CH₂—CH(CH₃)—CH₂—(2-methyl-1,3-propyl) and —CH₂—C(C₃)₂—CH₂—(2,2-dimethyl-1,3-propyl), or an alkyl-substituted or non-substituted octyl bridging group such as —CH₂—CH₂—CH₂—CH₂—CH₂—CH₂—CH₂—CH₂—(1,8-octyl) initiate polymerization of unsaturated monomers, preferably butadiene, at surprisingly higher polymerization temperatures with surprisingly lower amounts of dead initiator (higher efficiency) than similar initiators wherein A" is replaced by alkyl-substituted or non-substituted butyl, pentyl, or hexyl bridging groups, such as —CH₂—CH₂—CH₂—C₂—(1,4-butyl), —CH₂—CH₂—CH₂—CH₂—CH₂-(1,5-pentyl), or —CH₂—CH₂—CH₂—CH₂—CH₂—CH₂—(1,6-hexyl). For the purpose of this description, the number of carbon atoms in the bridging group refers to the carbons spanning the oxygen and lithium; i.e. alkyl branches on the bridging alkyl carbons, such as the methyl groups on the 2,2-dimethyl-1,3-propylene segment, are not counted.

In Structure (2), each R is preferably methyl and any alkyl branching on the bridging group A" is preferably methyl. Substituents other than alkyl groups may be useful for R and as branching on A" however the effect on initiation efficiency and polymerization temperature would have to be determined by experiments.

The efficiency of specific initiators appears to vary depending on the unsaturated monomer since some of the initiators have surprisingly improved performance for initiating polymerization of butadiene in comparison to isoprene. After initiation, the unsaturated monomers may be changed to form random or block copolymers without reducing the initiation efficiency. Suitable unsaturated monomers include conjugated diene hydrocarbons, such as butadiene and isoprene, and vinyl aromatic compounds, such as styrene.

The efficiency of initiators of this type can be readily determined by a variety of analytical methods. In living polymerizations, each mole of active initiator is expected to start one mole of polymer, so that the average molecular weight of the resulting polymer can be predicted from the following relationship:

(1)  $MW_{ave} = (m_{mono}/m_{init})(MW_{mono}) + MW_{init} + MW_{cap}$ where:

$m_{mono}$ = moles of monomer
$m_{init}$ = moles of initiator
$MW_{mono}$ = molecular weight of the monomer
$MW_{init}$ = MW of the fragment of the initiator that is incorporated into the polymer chain
$MW_{cap}$ = MW of the fragment of the capping reagent that is incorporated into the polymer chain If a fraction of the initiator charge fails to start polymer, the resulting product will be higher in molecular weight than predicted by equation (1). So long as that fraction remains inactive throughout the polymerization, the molecular weight distribution (MWD) will remain narrow and monodisperse, typical of a living polymerization having a faster rate of initiation than of propagation. In practice, molecular weights are often somewhat larger that predicted by equation (1) due to inactivation of a small fraction of the initiator charge by protic impurities present in monomers, solvents, etc.

A possible explanation for the observed difference in performance of the lithium initiators is that the bridging groups in the initiators of the present invention do not readily self-associate to form cyclic rings whereas the bridging groups of the remaining initiators are readily configured as cyclic rings. Assuming that cyclic ring formation results in dead initiator, the experimental results indicate that the initiators of the present invention experience little or no cyclic ring formation even at higher operating temperatures which render the other initiators substantially inactive. It is clear from the polymerization results that a significant fraction of the initiators with 4, 5 or 6 alkyl-carbon bridging groups is either consumed by side reactions before any polymerization begins or remains dormant throughout the polymerization. In addition to wasting valuable initiator, these processes may produce medium-molecular weight by-products that are hard to remove from the polymer and have an undesirable impact in applications such as coatings and food packaging where substances that contribute to the volatile organic carbon (VOC) of the product, and extractables, are undesirable.

The initiators of the present invention are similar to s-butyllithium with regard to economical operating temperature and low amounts of dead initiator. However the initiators of the invention have the advantage of placing a silyl ether group at the start of the polymer chain which serves as a "masked" or "protected" alcohol, capable of conversion to a primary alcohol group after polymerization is completed, as described in WO 91/12277. The polymer chains may be terminated, end-capped, or coupled by conventional means to end the polymerization and provide one or more terminal functional groups on linear or branched polymers containing polymerized conjugated dienes.

The lithium initiator process is well known as described in U.S. Pat. Nos. 4,039,593 and U.S. Pat. No. Re. 27,145 which descriptions are incorporated herein by reference. Typical living polymer structures that can be made with the initiators of Structure (2) include:

X—B—Li
X—B/A—Li
X—A—B—Li
X—B—A—Li
X—B—B/A—Li
X—B/A—B—Li
X—A—B—A—Li wherein B represents polymerized units of one or more conjugated diene hydrocarbons, A represents polymerized units of one or more vinyl aromatic compounds, B/A represents random polymerized units of the conjugated diene hydrocarbons and the vinyl aromatic monomers, and X is the residue of a lithium initiator such as sec-butyllithium. The living polymers are terminated as linear polymers, coupled to form branched polymers, or cappped to form additional functional groups by conventional means such as addition of methanol, silicon tetrachloride, divinylbenzene, or ethylene oxide. In the present invention, X is a silyl ether group and cleavage of the silyl ether leaves a primary alcohol group in this position.

The initiators of the present invention are very active at room temperature and polymerization is preferably initiated at a temperature from 20° C. to 60° C. most preferably from 30° C. to 40° C. It is generally advisable to keep the polymerization temperature below about 100° C.; above this temperature, side reactions that change microstructure and limit capping efficiency may become important. Polymerizations can be carried out over a range of solids, preferably from about 5% to about 80%, most preferably from about 10% to about 40%. For high solids polymerizations, it is preferable to add the monomer in increments to avoid exceeding the desired polymerization temperature. If the initiator is to be added to the full monomer charge, it is preferable to run the polymerization between 10% and 20% solids.

When the conjugated diene is 1,3-butadiene and when the conjugated diene polymer will be hydrogenated, the anionic polymerization of the conjugated diene hydrocarbons is typically controlled with structure modifiers such as diethyl ether or glyme (1,2-diethoxyethane) to obtain the desired amount of 1,4-addition. As described in U.S. Pat. No. Re 27,145 which is incorporated by reference herein, the level of 1,2-addition of a butadiene polymer or copolymer can greatly affect elastomeric properties after hydrogenation. The hydrogenated polymers exhibit improved heat stability and weatherability in the final, adhesive, sealant or coating.

The 1,2-addition of 1,3-butadiene polymers having terminal functional groups influences the viscosity of the polymers as described in more detail below. A 1,2-addition of about 40% is achieved during polymerization at 50° C. with about 6% by volume of diethyl ether or about 1000 ppm of glyme. Generally, vinyl contents in this range are desirable if the product is to be hydrogenated, while low vinyl contents are preferred if the polymer is to be used in its unsaturated form.

Anionic polymerization is often terminated by addition of water to remove the lithium as lithium hydroxide (LiOH) or by addition of an alcohol (ROH) to remove the lithium as a lithium alkoxide (LiOR). Polymers prepared from initiators of the present invention and terminated in this way will be monohydroxy functional (mono-ols) after removal of the silyl protecting group. To prepare polymers having an additional terminal functional groups, the living polymer chains are preferably terminated with hydroxyl, carboxyl, phenol, epoxy, or amine groups by reaction with ethylene oxide, oxetane, 2,2-dimethyloxetane, carbon dioxide, a protected hydroxystyrene monomer, ethylene oxide plus epichlorohydrin, or the amine compounds listed in U.S Pat. No. 4,791,174, respectively. For the preparation of telechelic diols, the preferred process is to terminate with 1-10 equivalents, most preferably 1-2 equivalents, of ethylene oxide at 30° C.-50° C. This reaction is quite rapid; reaction times from 5 to 30 minutes yield acceptable results.

The termination step can result in release of fine particles of lithium bases as described in U.S. Pat. No. 5,166,277 which is incorporated by reference herein. The lithium bases may interfere with hydrogenation of the polymer and preferably are removed, especially if the hydrogenation is to be carried out at high solids.

Termination with carbon dioxide results in carboxylate salt groups that reduce hydrogenation catalyst activity as described in U.S. Pat. No. 4,970,254 which disclosure is incorporated by reference herein. Improved hydrogenation is obtained by converting the carboxylate salt groups to ester groups prior to hydrogenation and then reconverting to carboxylate salt or carboxylic acid groups after hydrogenation.

Hydrogenation of at least 90%, preferably at least 95%, of the unsaturation in low molecular weight butadiene polymers is achieved with nickel catalysts as described in U.S. Pat. Nos. Re. 27,145 and 4,970,254 and U.S. patent application Ser. No. 07/785715 now U.S. Pat. No. 5,166,277 which are incorporated by reference herein. The preferred nickel catalyst is a mixture of nickel 2-ethylhexanoate and triethylaluminum described in more detail in the examples. It is preferable to extract the nickel catalyst after hydrogenation by stirring the polymer solution with aqueous phosphoric acid (20-30 percent by weight), at a volume ratio of about 0.5 parts aqueous acid to 1 part polymer solution, at about 50° C. for 30-60 minutes while sparging with a mixture of oxygen in nitrogen. This step is also described in more detail in the examples.

Saturated or unsaturated conjugated diene polymers having one or more terminal functional group selected from hydroxyl, carboxyl, phenol, epoxy, and amine groups can be used without solvents when the viscosity of the polymer is less than about 500 poise at mixing and application temperature. Linear hydrogenated butadiene or isoprene polymers having two terminal hydroxyl groups per molecule and lower viscosity than 500 poise at mixing and application temperatures are produced by limiting the peak molecular weight to a range from about 500 to 20,000 and by limiting the 1,2-addition of hydrogenated butadiene to an amount between 30% and 70%, preferably between 40% to 60%.

After polymerization and, optionally, hydrogenation and washing of the polymer, the silyl group at the front of the polymer chain is removed to generate the desired primary hydroxyl functional group. This step is often referred to as deprotection. A variety of processes for removal of the silyl protecting group are known; for a review, see T. W. Greene, "Protective Groups in Organic Synthesis" J. Wiley and Sons, New York, 1981, incorporated herein by reference. A preferable process would involve easily handled, relatively low toxicity, and inexpensive reagents. Reaction with tetrabutylammonium fluoride in THF, as described in WO 91 112277, would be disadvantage due to the high cost and toxicity of the reagents. In a preferred process, the silyl group is removed by reaction of the polymer solution with 1-10 equivalents (basis silyl end groups) of a strong organic acid, preferably methanesulfonic acid (MSA), in the presence of 0.1%-2% by weight of water and 5%-50% by volume of isopropanol (IPA) at about 50° C. Essentially complete conversion to the alcohol was observed for polymers produced using initiators that lacked β branching, such as Structure (2) having a 1,3-propylene bridging group, in 30 minutes to 3 hours using about 5 equivalents of MSA and about 15%-20% IPA. Polymers produced from Structure (2) having a 2,2-dimethyl-1,3-propylene bridging group (possess two methyl groups β to the silanol) required higher acid concentrations to achieve high levels of deprotection in a comparable period of time. Polymers prepared from an initiator of Structure (2) with a 2-methyl-1,3-propylene bridging group (possess one methyl group β to the silanol) would should be intermediate with respect to ease of deprotection.

Sufficient IPA must be present during deprotection to prevent the formation of a discrete aqueous phase. Excess acid is then removed by washing with dilute aqueous base, preferably 0.1N-0.5N sodium hydroxide, followed by water. For some applications, such as coatings prepared by baked cures of the polymer with amino resins in the presence of a strong organic acid catalyst, it may be preferable to use the polymer in its "protected" form. The viscosity of the protected polymer is lower and conditions such as those described above should accomplish the deprotection (generate the alcohol) during the cure.

The conjugated diene polymers produced as described above have the conventional utilities for terminally functionalized polymers of such as forming adhesives, coatings, and sealants. Additionally, the polymers may be used to modify polyurethanes, polyesters, polyamides, polycarbonates, and epoxy resins.

DETAILED DESCRIPTION OF PREFERRED EMBODIMENTS

The preferred process produces dihydroxylated 1,3-butadiene polymers having a peak molecular weight from 500 to 200,000, most preferably from 500 to 20,000. The dihydroxylated polymers can be unsaturated with 1,2-addition from 5% to 95% or hydrogenated with 1,2-addition from 30% to 70%. The polymers preferably have from 1.75 to 2.0, most preferably from 1.95 to 2.0, terminal hydroxyl groups per molecule.

The dihydroxylated polymers are preferably produced by initiation with a lithium initiator having Structure (2) wherein A'' is a non-substituted alkyl bridging group having 3 or 8 alkyl carbons. Most preferably the lithium initiator has the structure

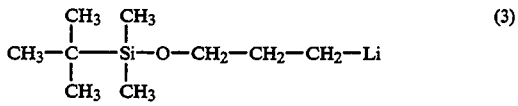  (3)

which is produced by silylation of 3-chloro-1-propanol, followed by reaction with lithium metal. After polymerization of the desired amount of 1,3-butadiene, the living polymer is capped with ethylene oxide and reacted with methanol to give a terminal primary alcohol group. The silyl group is then converted to a hydroxyl group by reaction with MSA in the presence of water and IPA.

The preferred polymers of the present invention are useful in adhesives (including pressure sensitive adhesives, contact adhesives, laminating adhesives and assembly adhesives), sealants (such as urethane architectural sealants, etc.), coatings (such as topcoats for automotive, epoxy primers for metal, polyester coil coatings, alkyd maintenance coatings, etc.), films (such as those requiring heat and solvent resistance), molded and extruded thermoplastic and thermoset parts (for example thermoplastic injection molded polyurethane rollers or reaction injection molded thermoset auto bumper, facie, etc.).

A composition of the instant invention may contain plasticizers, such as rubber extending plasticizers, or compounding oils or organic or inorganic pigments and dyes. Rubber compounding oils are well-known in the art and include both high saturates content oils and high aromatics content oils. Preferred plasticizers are highly saturated oils, e.g. Tufflo ® 6056 and 6204 oil made by Arco and process oils, e.g. Shellflex ® 371 oil made by Shell. The amounts of rubber compounding oil employed in the invention composition can vary from 0 to about 500 phr, preferably between about 0 to about 100 phr, and most preferably between about 0 and about 60 phr.

Optional components of the present invention are stabilizers which inhibit or retard heat degradation, oxidation, skin formation and color formation. Stabilizers are typically added to the commercially available compounds in order to protect the polymers against heat degradation and oxidation during the preparation, use and high temperature storage of the composition.

Various types of fillers and pigments can be included in the coating or sealant formulation. This is especially true for exterior coatings or sealants in which fillers are added not only to create the desired appeal but also to improve the performance of the coatings or sealant such as its weatherability. A wide variety of fillers can be used. Suitable fillers include calcium carbonate, clays, talcs, silica, zinc oxide, titanium dioxide and the like. The amount of filler usually is in the range of 0 to about 65% w based on the solvent free portion of the formulation depending on the type of filler used and the application for which the coating or sealant is intended. An especially preferred filler is titanium dioxide.

The dihydroxylated conjugated diene polymers of the present invention may also be blended with other polymers to improve their impact strength and/or flexibility. Such polymers are generally condensation polymers including polyamides, polyurethanes, vinyl alcohol polymers, vinyl ester polymers, polysulfones, polycarbonates and polyesters, including those, like polyacetones, which have a recurring ester linkage in the molecule, and those, like polyalkylene arylates, including polyalkylene terephthalates, having a structure formed by polycondensation of a dicarboxylic acid with a glycol. The blends may be made in the reactor or in a post compounding step.

The present invention is further described by the following examples which include the best mode known to Applicant for making a dihydroxylated, saturated polybutadiene (EB Diol). The examples are not intended to limit the present invention to specific embodiments although each example may support a separate claim which Applicant asserts to be a patentable invention.

The peak molecular weights were measured using gel permeation chromatography (GPC) calibrated with polybutadiene standards having known peak molecular weights. The solvent for the GPC analyses was tetrahydrofuran.

The 1,2-additions of polybutadiene were measured by $^{13}$C NMR in chloroform solution.

Initiator Synthesis

Initiators, designated PFI1–PFI6 were prepared in dry cyclohexane by reaction of the desired chloroalcohol with t-butyldimethylsilyl chloride (TBDMS-Cl) in the presence of imidazole, followed by reaction with lithium metal, as described in WO 91 112277. The initiator possessing a 2-methyl-1,3-propyl bridging group can be prepared in the same manner, from 3-chloro-2-methyl-1-propanol, which is available as the product of partial chlorination of 2-methyl-1,3-propane diol. The concentration of active lithium alkyl was determined by titration with diphenylacetic acid, as decried by W. G. Korfron and L. M. Baclawski (*J. Org. Chem*, 41(10), 1879 (1976)).

Polymerization

Unless otherwise specified, polymers prepared to study initiation efficiency were synthesized in a 2 liter glass autoclave (Büchi) at 10% solids, according to the following general procedure: Butadiene (100 g.) was added to a 90/10 mixture of cyclohexane/diethyl ether (900 g. total). The calculated quantity of initiator solution (typically about 12 to 15% wt.) was added to the monomer solution at 20° C.–23° C. and then the temperature was increased to 40° C. over about a 10 minute period, by setting the temperature of the circulating bath to 43.5° C.; temperature control is provided by circulating water from a temperature-controlled circulating bath, through a concentric jacket. Polymerizations that yielded the desired low-molecular weight products typically were sufficiently exothermic to increase the reactor temperature to at least 48$^{od}$. The polymerization was allowed to proceed for about 45 minutes and then 2-10 equivalents of the capping agent, either ethylene oxide (EO) or oxetane, was added to generate the terminal hydroxyl group. After about 30 minutes, the reaction was terminated with about 1.1 equivalents of methanol. Samples were analyzed by $^{13}$C NMR and GPC (calibrated with commercial poly(-butadiene) standards). All polymers exhibited a narrow molecular weight distribution. All polymers prepared in the presence of ether were determined to have resulted from about 40% 1,2 addition of butadiene. Capping efficiencies were generally high, at least 80%, and did not depend on the identity of the initiator.

EXAMPLE 1

A hydrogenated linear butadiene polymer having about two terminal hydroxyl groups per molecule, a peak molecular weight of 3,900, a 1,2-addition of butadiene of 40%, and a residual unsaturation of 0.17 meq/g (98.9% hydrogenated) is prepared as described below: 675 g. (12.5 moles) of butadiene, 450 g. of diethyl ether and 3375 g. of cyclohexane were charged into a 2 gal. stainless steel autoclave. The reactor was heated to 40° C. and 280 g. of a 10.9% wt. solution of PFI3 (the 1,3-propyl bridging group of structure 3 above) in cyclohexane (0.169 moles) was added; the heat of reaction increased the reactor temperature to about 45° C. After about 9 minutes, the reaction temperature was increase to about 50° C. and polymerization was allowed to continue for about 40 minutes. After 40 minutes, the reactor was cooled to about 40° C. and 31 g. (4 equivalents) of ethylene oxide was added. After 30 minutes, 6 g. (1.1 equivalents) of methanol was added. GPC analysis indicated a molecular weight of 3,900 amu., in good agreement with the targeted value of 4,000 amu.

The above polymer cement was charged into a 3 gal. high-pressure stainless steel autoclave, diluted to 9.5% solids by the addition of 2,597 g. of cyclohexane, and heated to 40° C. The reactor was sparged with hydrogen at a rate of about 0.6 SCFM, while maintaining a pressure of 800 psi. 70.8 mLs. of a 6700 ppm (Ni) solution of Ni/Al catalyst was charged to the reactor, resulting in an immediate exothermic reaction. The catalyst is prepared in advance by reacting nickel 2-ethylhexanoate with triethylaluminum in cyclohexane in amounts sufficient to give a ratio of 2.0 moles of aluminum to 1 mole of nickel. After peaking at about 90° C., the temperature decreased and was held at about 70° C. Analysis for residual unsaturation (ozone titration) indicated about 99% conversion after 120 minutes. The catalyst was extracted by washing the cement with two 500 ml. aliqouts of 20% aqueous phosphoric acid.

A solution containing 70 g. of water and 81 g. of anhydrous methanesulfonic acid in 1050 g. of isopropanol was added to the washed polymer cement (5500 g.). The resulting slightly hazy solution was stirred for 2 hours at about 50° C. The sample was washed with one aliquot of 0.1N aqueous sodium hydroxide and two aliquots of DI water (about 5.4 liters each); the pH of the aqueous phase after the second water wash was about 7. The polymer solvent was removed in a rotary evaporator, leaving a colorless, slightly hazy liquid. The sample was analyzed by High Performance Liquid Chromatography (HPLC) and $^{13}$C NMR, to determine the relative amounts of the desired dihydroxy material (diol), mono-hydroxy material (either capped with EO but not deprotected or deprotected but terminated by protic impurities) and non-functional material (protected-no EO incorporated). The HPLC separation was accomplished with a 250 mm×4.6 mm 5 micron DIOL phase column using a stepped heptane/tetrahydrofuran gradient. An evaporative light scattering detector is used to quantify the sample. These techniques indicate 98% and 97% conversion to the di-hydroxy product, respectively.

EXAMPLE 2

A hydrogenated linear butadiene polymer having about one terminal hydroxyl groups per molecule, a peak molecular weight of 1,900, a 1,2-addition of butadiene of 40%, and a residual unsaturation of 0.14 meq/g (99.2% hydrogenated) is prepared as described below: The unsaturated butadiene polymer was prepared by the polymerization of butadiene with PFI3 (1,3-propyl bridging group) as the initiator in a glass autoclave, as described in the General Procedure. Methanol was added following polymerization of the butadiene, resulting in a polymer with the silyl ether group (protected alcohol) at one end, an a proton at the other. This polymer corresponds to entry 3I in Table 3.

The polymer solution was then transferred to a high pressure reactor for hydrogenation using a Nickel-/Aluminum catalyst. The catalyst is prepared in advance by reacting nickel 2-ethylhexanoate with triethylaluminum in cyclohexane in amounts sufficient to give a ratio of 2.5 moles of aluminum to 1 mole of nickel. The polymer solution is sparged with hydrogen at 40° C. The reactor is then filled with hydrogen to a pressure of 7000 psig. An aliquot of the Ni/Al catalyst solution, sufficient to bring the nickel concentration in solution to 50 ppm., is then pressured into the reactor. An exothermic hydrogenation reaction ensues. Ozone titration indicated 99.2% hydrogenation of the butadiene unsaturation (final R.U.=0.14 meq/g).

The catalyst residues were extracted by contacting the resulting solution with aqueous phosphoric acid in a 1 l. resin kettle equipped with a mechanical stirrer at 50° C. Five equivalents of MSA was then added to the washed solution, along with sufficient IPA as to afford a concentration of ten weight percent IPA in the reaction mixture. This solution was heated at 50° C. for 3 hours, washed with aqueous base, and then water, and then finished in a rotary evaporator, as described above. The sample was then analyzed by $^{13}$C NMR and HPLC, as described above. These techniques indicate 93% and 94% conversion to the mono-hydroxy product, respectively.

EXAMPLE 3

A linear butadiene polymer having about two terminal hydroxyl group per molecule, a peak molecular weight of 3,900, and a 1,2-addition of 7%, was prepared as described below: Butadiene was polymerized with PFI3 (1,3-propyl bridging group) in a glass autoclave, as described in the General Procedure, except cylcohexane, rather than a mixture of cyclohexane and diethyl ether, was used as the solvent. Ethylene oxide was added following polymerization of the butadiene, and the polymerization was terminated with methanol, resulting in a polymer with the silyl ether group (protected alcohol) at one end, a primary alcohol group at the other. This polymer corresponds to entry 3J in Table 3.

Five equivalents of MSA was then added to the washed solution, along with sufficient IPA and water as to afford a concentration of fifteen weight percent IPA and one weigh percent water in the reaction mixture. This solution was heated at 50° C. for 2 hours, washed with aqueous base, and then water, and then finished in a rotary evaporator, as described above. The sample was then analyzed by $^{13}C$ NMR and HPLC, as described above. These techniques indicate 98% and 99% conversion to the di-hydroxy product, respectively.

EXAMPLE 4

A linear butadiene polymer having about two terminal hydroxyl group per molecule, a peak molecular weight of 4,400, and a 1,2-addition of 40%, was prepared as described below: Butadiene was polymerized with PFI3 in a glass autoclave, as described in the General Procedure. Ethylene oxide was added following polymerization of the butadiene, and the polymerization was terminated with methanol, resulting in a polymer with the silyl ether group (protected alcohol) at one end, a primary alcohol group at the other. This polymer corresponds to entry 2H in Table 2.

Ten equivalents of MSA was then added to the washed solution, along with sufficient IPA and water as to afford a concentration of 42 weight percent IPA and about 0.6 weight percent water in the reaction mixture. This solution was heated at 50° C. for a total of 19 hours; samples were taken at 1, 2 and 3 hours. The final product was washed with aqueous base, and then water, and then finished in a rotary evaporator, as described above. HPLC analysis of each sample indicated that the ultimate conversion, to about 98% diol, had been achieved in 3 hours.

Tables 1–6 summarize the results of polymerizations with initiators possessing a variety of bridging alkyl groups structures. Initiation and polymerization was generally carried out at or above room temperature and examples are provided where polymerizations were carried out with and without the ether cosolvent. The last column tabulates "initiation efficiency", which is a measure of how well equation (1) predicts the observed molecular weight. It is readily apparent from these tables that the two initiators with three alkyl carbons in the bridging groups, designated PFI2 (2,2-dimethyl-1,3-propyl bridging group) and PFI3 (1,3-propyl bridging group), and the initiator with eight alkyl carbons in the bridging group, designated PFI6, are significantly more efficient initiators than those possessing from four to six alkyl carbons in the bridging groups (PFI1, PFI4 and PFI5). The efficiency of the 1,5-pentyl bridging group structure (PFI5) was moderately good (40%–60%), while the initiation efficiency of the hexyl containing initiator of WO 91 112277, PFI1, was generally poor (in most cases <40%). Initiation efficiency was poor for PFI1 even at 10° C. in the absence of ether (Example 1F).

TABLE 1

PFI1-Initiated Polymer Analytical Data (n-hexyl) (Comparison)

| # | Calc. MW | Capping Reagent | GPC MW | Initiation Efficiency[10] |
|---|---|---|---|---|
| 1A[1] | 5,270 | oxetane | 9,960 | 53% |
| 1B[2] | 6,400 | EO | 12,280 | 52% |
| 1C[2] | 4,320 | EO | 15,430 | 28% |
| 1D[3] | 4,290[6] | oxetane | 13,800 | 31% |
| 1E[3] | 1,490[7] | oxetane | 3,900 | 38% |
| 1F[3] | 4,290[8] | oxetane | 15,700 | 27% |
| 1G[3] | 4,460 | oxetane | 15,400 | 29% |
| 1H[4] | 4,290 | oxetane | 16,400 | 26% |
| 1I[4] | 3,880[9] | oxetane | 16,800 | 23% |

[1]titrated initiator conc. 21% wt.; polymerized at 6.5% solids.
[2]titrated initiator conc. 12.5% wt.
[3]titrated initiator conc. 13.1% wt.
[4]titrated initiator conc. 12.7% wt.
[5]polymerized at 7.3% solids.
[6]isoprene, no ether.
[7]isoprene, 10% ether.
[8]Initiate at 10° C., 1hr., no ether.
[9]Initiated at 30° C.
[10]$(MW_{target}/MW_{GPC}) \times 100$

TABLE 2

PFI2-Initiated Polymer Analytical Data (2,2-dimethyl-1,3-propyl)

| # | Calc. MW | Capping Reagent | GPC MW | Initiation Efficiency[7] |
|---|---|---|---|---|
| 2A[1] | 4,880 | oxetane | 4,800 | 102.%[6] |
| 2B[1] | 4,690 | EO | 5,000 | 94% |
| 2C[1] | 5,140[4] | EO | 5,500 | 93% |
| 2D[2] | 5,280[4] | oxetane | 5,700 | 93% |
| 2E[3] | 4,090 | oxetane | 4,160 | 98% |
| 2F[3] | 1,810 | oxetane | 1,770[5] | 102.%[6] |
| 2G[3] | 1,560 | oxetane | 1,470 | 106%[6] |
| 2H[1] | 4,000 | EO | 4,400 | 91% |

[1]titrated initiator conc. 11.4% wt.
[2]titrated initiator conc. 9.6% wt.
[3]titrated initiator conc. 13.5% wt.
[4]isoprene, no ether.
[5]Polymerized at 6.5% solids.
[6]Values greater than 100% reflect the level of accuracy in MW determination.
[7]$(MW_{target}/MW_{GPC}) \times 100$.

TABLE 3

PFI3-Initiated Polymer Analytical Data (n-propyl)

| # | Calc. MW | Capping Reagent | GPC MW | Initiation Efficiency[7] |
|---|---|---|---|---|
| 3A[1] | 4,210 | oxetane | 4,200 | 100% |
| 3B[1,3] | 3,940 | oxetane | 5,800 | 68% |
| 3C[1,3] | 3,980 | oxetane | 6,100 | 65% |
| 3D[1] | 3,920 | oxetane | 4,200 | 93% |
| 3E[2] | 4,050 | oxetane | 4,300 | 94% |
| 3F[2] | 1,540 | oxetane | 1,800 | 86% |
| 3G[2] | 4,000 | EO | 5,600[4] | 71% |
| 3H[2] | 3,830 | EO | 4,700 | 82% |
| 3I[2] | 1,500 | H | 1,900 | 79% |
| 3J[5] | 4,000 | EO | 3,900 | 102%[6] |

[1]titrated initiator conc. 15.0% wt.
[2]titrated initiator conc. 14.3% wt.
[3]Reaction temperature maintained below 55° C.
[4]polymerized at 15% solids.
[5]butadiene, no ether.
[6]Values greater than 100% reflect the level of accuracy in MW determination.
[7]$(MW_{target}/MW_{GPC}) \times 100$.

TABLE 4

PFI4-Initiated Polymer Analytical Data (n-buty) (Comparison)

| # | Calc. MW | Capping Reagent | GPC MW | Initiation Efficiency[4] |
|---|---|---|---|---|
| 4A[1,2] | 4,000 | EO | 24,000 | 17% |

TABLE 4-continued

PFI4-Initiated Polymer Analytical Data (n-butyl) (Comparison)

| # | Calc. MW | Capping Reagent | GPC MW | Initiation Efficiency[4] |
|---|---|---|---|---|
| 4B[1,3] | 3,990 | EO | 11,700 | 34% |

[1] titrated initiator conc. 10.4% wt.
[2] initiation temperature = 20° C., 10% solids.
[3] initiation temperature = 30° C., 13.5% solids.
[4] (MW$_{target}$/MW$_{GPC}$) X 100.

TABLE 5

PFI5-Initiated Polymer Analytical Data (n-pentyl) (Comparison)

| # | Calc. MW | Capping Reagent | GPC MW | Initiation Efficiency[5] |
|---|---|---|---|---|
| 5A[1,2] | 4,190 | EO | 6,600 | 63% |
| 5B[1,3] | 4,270 | EO | 8,000 | 53% |
| 5C[1,4] | 4,060 | EO | 9,500 | 43% |
| 5D[1,2] | 4,000 | EO | 9,800 | 41% |

[1] titrated initiator conc. 17.5% wt.
[2] initiation temperature = 30° C., 15% solids.
[3] initiation temperature = 25° C., 10% solids.
[4] initiation temperature = 40° C., 10% solids.
[5] (MW$_{target}$/MW$_{GPC}$) X 100.

TABLE 6

PFI6-Initiated Polymer Analytical Data (n-octyl)

| # | Target MW | Capping Reagent | GPC MW | Initiation Efficiency[5] |
|---|---|---|---|---|
| 6A[1,2] | 4,000 | EO | 4,600 | 87% |
| 6B[1,3] | 4,000 | EO | 4,600 | 87% |
| 6C[1,4] | 4,000 | EO | 4,400 | 91% |

[1] titrated initiator conc. 19.1% wt.
[2] initiation temperature = 30° C., 15% solids.
[3] initiation temperature = 30° C., 10% solids.
[4] initiation temperature = 20° C., 10% solids.
[5] (MW$_{target}$/MW$_{GPC}$) X 100.

In the examples of WO 91 112277, initiation is carried out at −5° C. for one hour, in the absence of ether. Most surprisingly, PFI3 was found to initiate polymerization more efficiently at 30° C. than at 20° C.; comparing entries 3B and 3C with the others in Table 3.

We claim:

1. A process for making functionalized polymers, comprising the steps of:
    initiating polymerization of an unsaturated monomer at a temperature from 20° C. to 60° C. with a lithium initiator having the structure

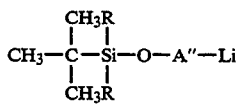

wherein each R is methyl, ethyl, n-propyl, or n-butyl and A″ is an alkyl-substituted or non-substituted propyl bridging group or an alkyl-substituted or non-substituted octyl bridging group; and
    recovering a linear or branched polymer having one or more terminal functional groups.

2. The process of claim 1, wherein polymerization is initiated at a temperature from 30° C. to 40° C.

3. The process of claim 1, further comprising the step of reacting the polymer with ethylene oxide prior to recovering the polymer.

4. The process of claim 1, further comprising the step of reacting the recovered polymer with methanesulfonic acid to convert silyl ether groups to hydroxyl groups.

5. The process of claim 1, wherein A″ is non-substituted propyl or non-substituted octyl.

6. The process of claim 1 wherein the lithium initiator has the structure

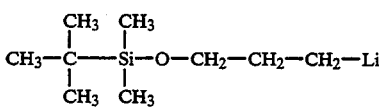

7. The process of claim 1, wherein the initiator initiates polymerization of butadiene.

8. The process of claim 7, further comprising the step of hydrogenating unsaturation in the butadiene polymer prior to recovery.

9. A process for making a terminally functionalized polymer, comprising the steps of:
    initiating polymerization of butadiene at a temperature from 30° C. to 50° C. with a lithium initiator having the structure

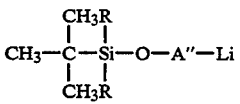

wherein A″ is a non-substituted propyl bridging group or non-substituted octyl bridging group;
    reacting the polymer with ethylene oxide;
    reacting the polymer with methanesulfonic acid to convert existing silyl ether groups to hydroxyl groups; and
    recovering a linear polymer having about two terminal hydroxyl groups per molecule.

10. The process of claim 9, further comprising the step of hydrogenating the polymer prior to recovery.

11. The process of claim 9, wherein the lithium initiator has the structure

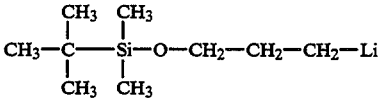

12. The process of claim 11, wherein the lithium initiator polymerizes only 1,3-butadiene.

* * * * *